(12) United States Patent
Lichtenstein et al.

(10) Patent No.: US 9,980,653 B2
(45) Date of Patent: May 29, 2018

(54) VALVE VIEW MAP

(71) Applicant: BIOSENSE WEBSTER (ISRAEL), LTD., Yokneam (IL)

(72) Inventors: Yoav Lichtenstein, Raanana (IL); Fady Massarwa, Baka El Gharbiya (IL)

(73) Assignee: BIOSENSE WEBSTER (ISRAEL), LTD., Yokneam (IL)

( * ) Notice: Subject to any disclaimer, the term of this patent is extended or adjusted under 35 U.S.C. 154(b) by 380 days.

(21) Appl. No.: 13/886,376

(22) Filed: May 3, 2013

(65) Prior Publication Data
US 2014/0330111 A1    Nov. 6, 2014

(51) Int. Cl.
| | |
|---|---|
| *A61B 5/02* | (2006.01) |
| *G06T 11/20* | (2006.01) |
| *G06T 19/00* | (2011.01) |
| *A61B 5/06* | (2006.01) |
| *G06T 15/10* | (2011.01) |

(52) U.S. Cl.
CPC .......... *A61B 5/02* (2013.01); *A61B 5/06* (2013.01); *G06T 11/206* (2013.01); *G06T 15/10* (2013.01); *G06T 19/00* (2013.01); *G06T 2210/41* (2013.01); *G06T 2219/021* (2013.01)

(58) Field of Classification Search
None
See application file for complete search history.

(56) References Cited

U.S. PATENT DOCUMENTS

| | | | | |
|---|---|---|---|---|
| 5,107,444 A | * | 4/1992 | Wu | .......... G06T 17/20 345/419 |
| 2005/0004516 A1 | * | 1/2005 | Vanney | ...................... 604/95.05 |
| 2005/0038333 A1 | * | 2/2005 | Sra | .................................. 600/374 |
| 2005/0122236 A1 | * | 6/2005 | Brauer et al. | ............ 340/995.24 |
| 2008/0009758 A1 | * | 1/2008 | Voth | ...................... A61B 5/042 600/523 |
| 2008/0188765 A1 | * | 8/2008 | Stolarski et al. | ............. 600/518 |
| 2008/0281182 A1 | * | 11/2008 | Rabben et al. | ............... 600/407 |
| 2009/0069704 A1 | * | 3/2009 | MacAdam | ............. A61B 5/044 600/523 |
| 2010/0286550 A1 | * | 11/2010 | Harlev | ................. A61B 5/0536 600/547 |

(Continued)

FOREIGN PATENT DOCUMENTS

GB    2266214    10/1993

OTHER PUBLICATIONS

"Zygote Heart 3.0 Anterior Cut 3D Model" Archived on Jul. 10, 2010. Retrieved from http://web.archive.org/web/20100730225729/http://www.3dscience.com/3D_Models/Human_Anatomy/Heart/Heart_3_Anterior_Cut.php>.*

(Continued)

*Primary Examiner* — Zhengxi Liu
(74) *Attorney, Agent, or Firm* — Dergosits & Noah LLP; Todd A. Noah

(57) ABSTRACT

A method, including generating a three-dimensional (3D) map as a plurality of points illustrating a characteristic of a 3D heart chamber, the 3D heart chamber having an opening bounded by a perimeter. The method further includes transforming the perimeter into a closed two-dimensional (2D) figure having an interior. The plurality of points illustrating the characteristic are projected onto the interior of the 2D figure so as to generate a 2D map of the characteristic of the 3D heart chamber.

22 Claims, 10 Drawing Sheets

(56) References Cited

U.S. PATENT DOCUMENTS

2012/0230570 A1 9/2012 Zheng et al.

OTHER PUBLICATIONS

"Lesson: The Heart of the Matter" Archived on Jun. 9, 2012. Retrieved on Jun. 11, 2015 from <http://web.archive.org/web/20120609084617/http://www.teachengineering.org/view_lesson.php?url=collection/cub_/lessons/cub_human/cub_human_lesson05.xml>.*
Gyöngyösi, Mariann, et al. "NOGA-guided analysis of regional myocardial perfusion abnormalities treated with intramyocardial injections of plasmid encoding vascular endothelial growth factor A-165 in patients with chronic myocardial ischemia subanalysis of the Euroinject-One multicenter double-blind randomized study." Circulation 112.9 suppl (2005).*
"Anatomy of the Heart" http://www.biosbcc.net/b100cardio/htm/heartant.htm. Archived on Mar. 11, 2005. Retrieved on Dec. 2, 2015 from <https://web.archive.org/web/20050311213342/http://www.biosbcc.net/b100cardio/htm/heartant.htm>.*
Welukar "MitraClip: A New Approach for Managing Valvular Heart Diseases" Published on Dec. 20, 2011. Retrieved from http://www.hivehealthmedia.com/mitraclip-approach-managing-valvular-heart-diseases/ on Dec. 4, 2015.*
Volcano, "Volcano VIBE RX Integrates Intravascular Ultrasound With Balloon Catheter", Jun. 1, 2010, retrieved from http://www.medgadget.com/2010/06/volcano_vibe_rx_integrates_intravascular_ultrasound_with_balloon_catheter.html on Feb. 6, 2017.*
European Search Report dated Aug. 13, 2015 for corresponding Application No. EP14166920.0.

\* cited by examiner

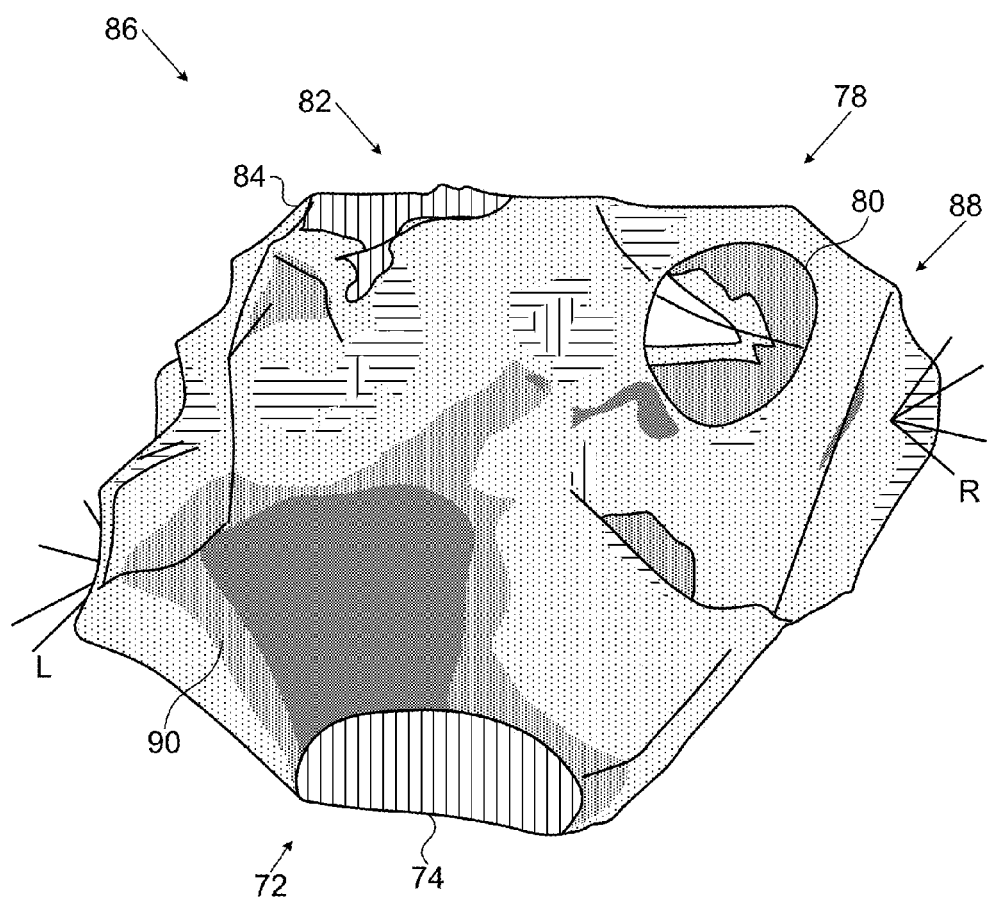
FIG. 2B

| | DARK BLUE |
| | LIGHT BLUE |
| | GREEN |
| | ORANGE/YELLOW |
| | RED |

≡ LIGHT BLUE
⋮ GREEN
▓ RED

VALVE VIEW MAP

FIELD OF THE INVENTION

The present invention relates generally to visualization of a body organ, and specifically to visualization of a heart of a patient.

BACKGROUND OF THE INVENTION

During a medical procedure, particularly an invasive medical procedure such as an investigation of the heart using a catheter inserted into the heart, there is a considerable amount of relevant information that an operator of the procedure must assimilate. There is usually very little time available to the operator to perform such assimilation. A system to simplify the presentation of such information would therefore be advantageous.

SUMMARY OF THE INVENTION

An embodiment of the present invention provides a method, including:

generating a three-dimensional (3D) map as a plurality of points illustrating a characteristic of a 3D heart chamber, the 3D heart chamber having an opening bounded by a perimeter;

transforming the perimeter into a closed two-dimensional (2D) figure having an interior; and projecting the plurality of points illustrating the characteristic onto the interior of the 2D figure so as to generate a 2D map of the characteristic of the 3D heart chamber.

The heart chamber may be a left atrium of a heart. Typically the opening includes a mitral valve, when open, of the heart. Alternatively, the opening includes a pulmonary vein opening to the left atrium.

In a disclosed embodiment the characteristic consists of one of a local activation time (LAT) of the heart chamber, a force acting on the heart chamber, and a temperature of the heart chamber.

The closed two-dimensional figure may be a circle.

In a further disclosed embodiment the plurality of points form a 3D mesh of line segments and junctions having a connectivity, and projecting the plurality of points includes projecting the 3D mesh to a 2D mesh while maintaining the connectivity of the 3D mesh in the 2D mesh, and generating the 2D map from the 2D mesh.

In a yet further disclosed embodiment the 2D map defines a plane, and the 2D map is rotatable about a line in the plane so as to present a perspective view of the 2D map, and a first region in contact with a first side of the plane corresponds to an interior region of the 3D heart chamber, and a second region in contact with a second side of the plane corresponds to an exterior region of the 3D heart chamber.

A distal end of a catheter may be located in the interior region at a distance and having an orientation with respect to the 3D heart chamber, and an icon representative of the distance and the orientation may be positioned in the first region with respect to the plane.

In an alternative embodiment the 3D heart chamber includes a left atrium, and a pulmonary vein connects to the exterior region of the left atrium via a vein opening, and the method further includes generating in the 2D map an indication of the vein opening, and positioning in the second region a representation of the pulmonary vein connected to the indication.

A distal end of a catheter may be located within the pulmonary vein, and an icon representative of a distance and a location of the distal end may be positioned within the second region.

In a further alternative embodiment the method includes incorporating an indication of respective tissue thicknesses of elements of the heart chamber into the 2D map.

There is further provided, according to an embodiment of the present invention, apparatus, including:

a processor which is configured to:

generate a three-dimensional (3D) map as a plurality of points illustrating a characteristic of a 3D heart chamber, the 3D heart chamber having an opening bounded by a perimeter, transform the perimeter into a closed two-dimensional (2D) figure having an interior, and project the plurality of points illustrating the characteristic onto the interior of the 2D figure so as to generate a 2D map of the characteristic of the 3D heart chamber; and a screen, upon which the processor is configured to display the 2D map.

The present disclosure will be more fully understood from the following detailed description of the embodiments thereof, taken together with the drawings, in which:

BRIEF DESCRIPTION OF THE DRAWINGS

FIG. 2B is a schematic 3D map produced from the mesh, according to embodiments of the present invention;

DETAILED DESCRIPTION OF EMBODIMENTS

Overview

Figure 1:
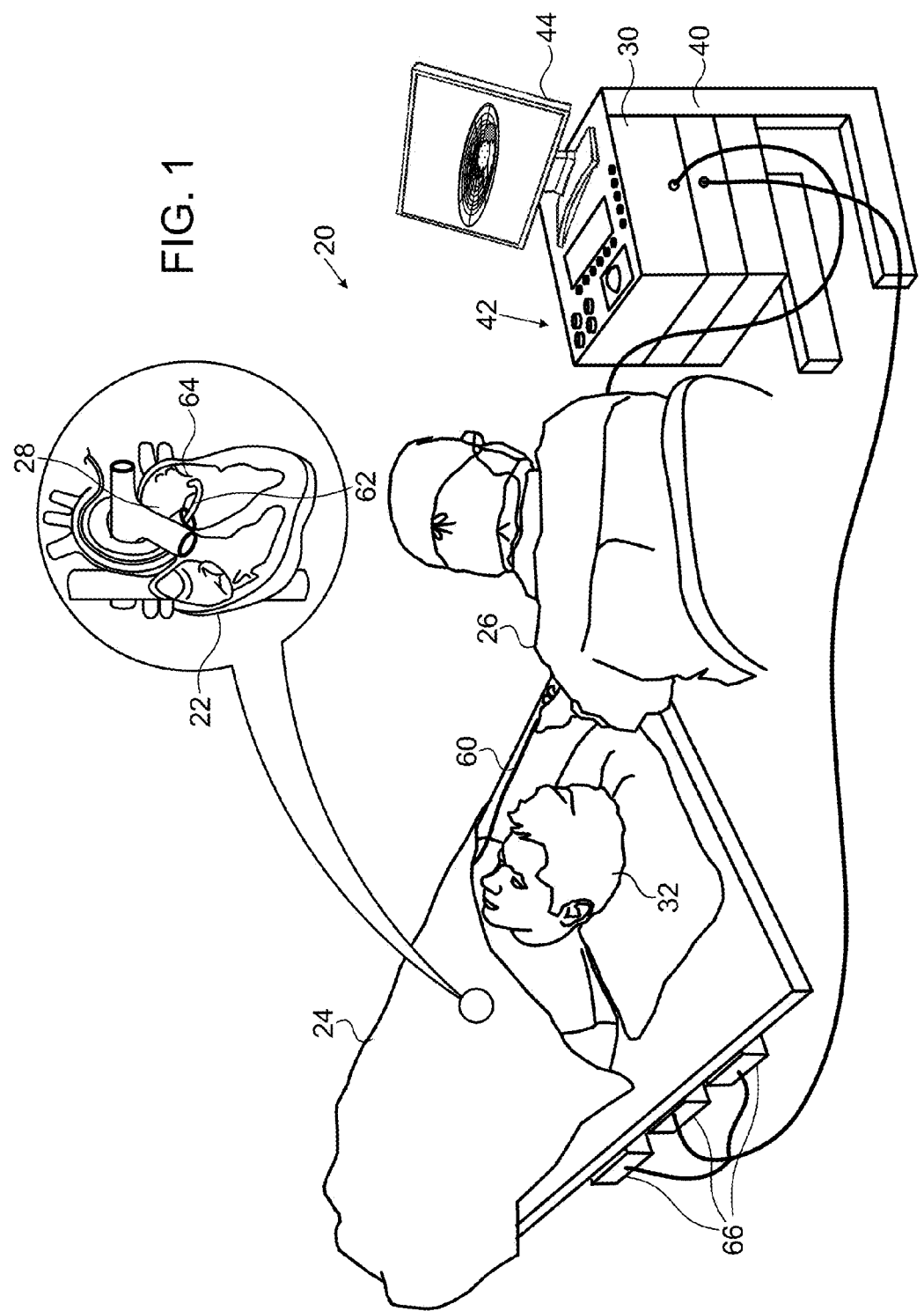
FIG. 1 is a schematic illustration of an organ visualization system, according to an embodiment of the present invention.

An embodiment of the present invention provides a method for viewing a characteristic of a chamber of the heart as a two-dimensional (2D) map. The 2D map simplifies the presentation of the characteristic, compared to its presentation in a three-dimensional (3D) format.

In order to formulate the 2D map, a 3D map of the characteristic is first generated. Typically, although not necessarily, the characteristic comprises a local activation time (LAT), and in the following description the characteristic is assumed to be the LAT. The 3D map is generated by determining locations and LATs at the locations, typically by inserting a catheter into the heart chamber. The catheter is tracked to determine locations of regions of the chamber, and acquires electrical signals that are used to calculate the LATs of the regions. The 3D map is typically generated from a 3D mesh of the locations, with values of the LATs incorporated into the 3D mesh.

The heart chamber has multiple openings which are visible in the 3D map and in the 3D mesh, and one of these openings, herein also termed the defining opening, is used as a basis for preparing the 2D map. The defining opening has a perimeter, and the perimeter is transformed into a closed 2D figure, for example a circle.

Elements from the 3D map, typically line segments and junctions of the 3D mesh, are projected onto the interior of the closed 2D figure, and the projected elements are used to formulate the 2D map of the LAT of the heart chamber.

In one embodiment the heart chamber is the left atrium, and the defining opening of the left atrium is selected to be the open mitral valve. From the point of view of the mitral valve, the left atrium is a "dome-like" structure, and the 2D map effectively projects the dome-like structure to a 2D plane.

The 2D map may be presented on a screen, and typically elements may be added to the map to assist a professional performing an invasive procedure on the chamber to better visualize the chamber. For example, the 2D map may be rotated to indicate an upper and lower surface of the map. Above the upper surface corresponds to inside the chamber; below the lower surface corresponds to outside the chamber. An icon representing the distal end of the catheter may be positioned above the map, i.e. inside the chamber. Elements representing connections to the chamber, such as a pulmonary vein in the case of the left atrium, may be drawn below the map, i.e., outside the chamber. The element representing the vein may be drawn connected to the vein opening of the 2D map.

In some embodiments additional features may be incorporated into the 2D map. For example, in a 2D map displaying values of LATs, tissue thickness of locations of the map may be indicated. The indication may be numerical, or could be by adding height changes above the plane of the 2D map, or shading or other markings onto the map. As another example, locations where ablation has been performed may be marked on the 2D map.

System Description

Reference is now made to FIG. 1, which is a schematic illustration of an organ visualization system 20, according to an embodiment of the present invention. In the following description, system 20 is assumed to be implemented, by way of example, during a medical procedure on a heart 22 of a patient 24. The procedure is performed by a medical professional 26, also herein assumed to operate system 20, and professional 26 is also referred to herein as operator 26. System 20 presents images of a cavity, such as an internal chamber of heart 22, allowing operator 26 to visualize characteristics of the cavity. While the description hereinbelow is directed to visualization of characteristics of a left atrium 28 of heart 22, it will be appreciated that system 20 may be used for visualization of characteristics of other chambers of the heart.

System 20 may be controlled by a system processor 30 which may be realized as a general purpose computer. Processor 30 may be mounted in a console 40, comprising operating controls 42 that typically include a keypad and a pointing device such as a mouse or trackball that operator 26 uses to interact with the processor. Results of the operations performed by processor 30 are provided to the operator on a screen 44 connected to the processor. Screen 44 typically also presents a graphic user interface to the operator enabling the operator to control system 20. Operator 26 is able to use controls 42 to input values of parameters used by processor 30 in the operation of system 20.

Processor 30 uses computer software to operate system 20. The software may be downloaded to processor 30 in electronic form, over a network, for example, or it may, alternatively or additionally, be provided and/or stored on non-transitory tangible computer-readable media, such as magnetic, optical, or electronic memory.

In operating system 20, professional 26 inserts a catheter 60 into patient 24, so that a distal end 62 of the catheter enters left atrium 28 of the patient's heart via a mitral valve 64. Processor 30 tracks distal end 62, typically both the location and the orientation of the distal end, while it is within heart 22. While the processor may use any method for tracking catheters known in the art, typically using an appropriate position sensor in the distal end, in the present description, for clarity and simplicity, processor 30 is assumed to use a magnetic tracker, such as is provided by the Carto® system produced by Biosense Webster, of Diamond Bar, Calif. In this case processor 30 operates magnetic field transmitters 66 in the vicinity of patient 24, so that magnetic fields from the transmitters interact with one or more tracking coils, located in distal end 62, forming a distal end position sensor. The coils interacting with the magnetic fields generate signals which are transmitted to processor 30, and the processor analyzes the signals to determine the location and orientation of distal end 62.

In addition to the tracking coils in distal end 62, the distal end typically comprises other sensors which measure characteristics of the region wherein the distal end is located. Examples of such sensors include one or more electrodes for measuring electro-potentials, a force sensor measuring the force exerted by the distal end on an object with which it is in contact, and a thermometer measuring a temperature of the distal end and/or of its surroundings. Typically, processor 30 integrates the output of these sensors with the locations and/or orientations of the distal end in order to produce, inter alia, maps comprising values of the characteristics overlaid onto a three-dimensional map of the locations of distal end 62.

Hereinbelow distal end 62 is assumed to comprise electrodes measuring electropotentials of locations of positions within left atrium 28 contacted by the electrodes. Processor 30 acquires these electropotentials, and calculates local activation times (LATs) for each of the measured locations within the left atrium.

Figure 2A:
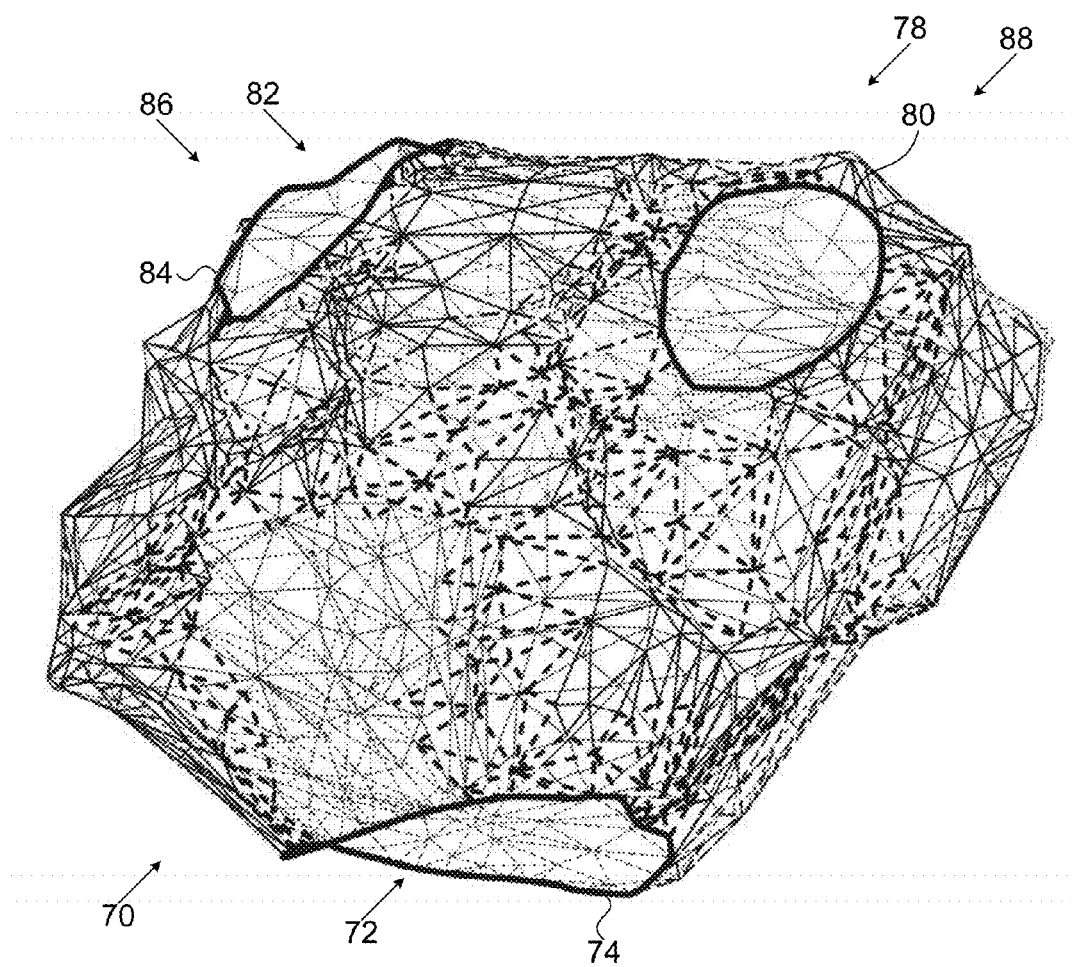
FIG. 2A is a schematic view of a three-dimensional (3D) mesh.
Figure 2A:
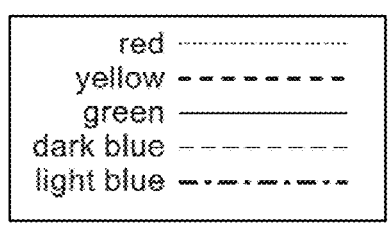

FIG. 2A is a schematic view of a three-dimensional (3D) mesh 70 illustrating calculated LATs, and FIG. 2B is a schematic 3D map 90 produced from the mesh, according to embodiments of the present invention.

Processor 30 produces 3D mesh 70 by evaluating 3D locations of a number of points on the surface of left atrium 28, and also by measuring or calculating values of the LATs at these points. From the evaluated 3D locations, processor 30 generates a 3D mesh of line segments joining points (corresponding to the evaluated locations), using any mesh generating method known in the art. Hereinbelow, by way of example and for simplicity, the mesh produced is assumed to be a mesh of triangles, and the mesh generating method is assumed to be the ball-pivoting algorithm. In some embodiments processor 30, under direction of operator 26 who may typically use controls 42, defines regions of the mesh which are assumed to be openings within the mesh. The openings are defined by a closed perimeter, and within the perimeter the processor does not generate line segments. The openings typically correspond to openings in left atrium 28. Thus, in the example illustrated by FIG. 2A, the 3D mesh has an opening 72 with a 3D perimeter 74, corresponding to mitral valve 64 when it is open. In addition, the mesh has an opening 78 bounded by a 3D perimeter 80, and an opening 82 bounded by a 3D perimeter 84. Openings 78 and 82 correspond to two of the pulmonary vein openings to the left atrium. There are two other openings, openings 86 and 88 at the "back" of the mesh, corresponding to the other two pulmonary vein openings to the left atrium.

The values of the LATs are then incorporated into the mesh by coloring line segments and/or junctions of the mesh with colors corresponding to the measured LAT values. The incorporation of the colors into the 3D mesh produces 3D colored mesh 70 of colored line segments and colored junctions. The different colors are illustrated schematically in FIG. 2A by different types of lines.

To produce 3D map 90 (FIG. 2B) processor 30 fills in the spaces between the line segments of 3D mesh 70 with appropriate colored surfaces, to generate the 3D map as a 3D surface. The 3D surface has substantially the same openings, with corresponding perimeters, as the openings of the 3D mesh. Thus, 3D map 90 is illustrated as having 3D openings 72, 78, 82, 86, and 88, and 3D perimeters 74, 80, and 84 of openings 72, 78, and 82 are shown. The perimeters of openings 86 and 88 are not shown in FIG. 2B, since they are at the "back" of the map.

The different colors of 3D map 90 are illustrated schematically in FIG. 2B by different types of shading. Typically, after the processor has produced the map, the map may be presented to operator 26 on screen 44, and the operator may use controls 42 to rotate the map to a desired orientation. In FIGS. 2A and 2B the orientations of 3D mesh 70 and 3D map 90 are slightly different, so that, for example, perimeters 74, 80, and 84 appear slightly different in the two figures.

In the view illustrated by FIG. 2B opening 72, corresponding to open mitral valve 64, and opening 78, corresponding to one of the pulmonary vein openings, are visible. The other three pulmonary vein openings 82, 86, and 88 are not visible in the view of FIG. 2B, but typically may be viewed by operator 26 rotating map 90 using controls 42.

Map 90 is presented on screen 44 as an external three-dimensional view of the LATs of the left atrium. Consequently, portions of the LATs, that would normally be on the "back" side of the view and thus not be visible, are visible through openings 72 and 78.

Figure 3A:
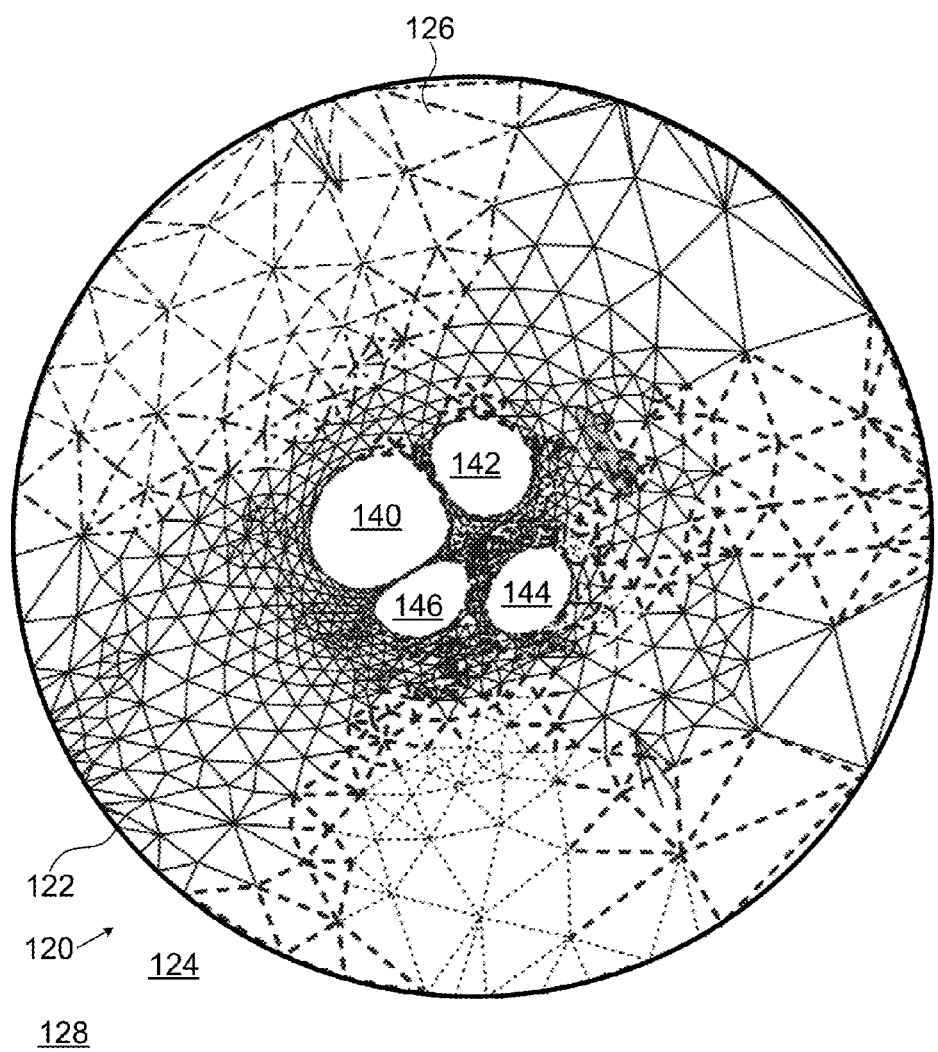
FIG. 3A is a schematic two-dimensional (2D) mesh.
Figure 3B:
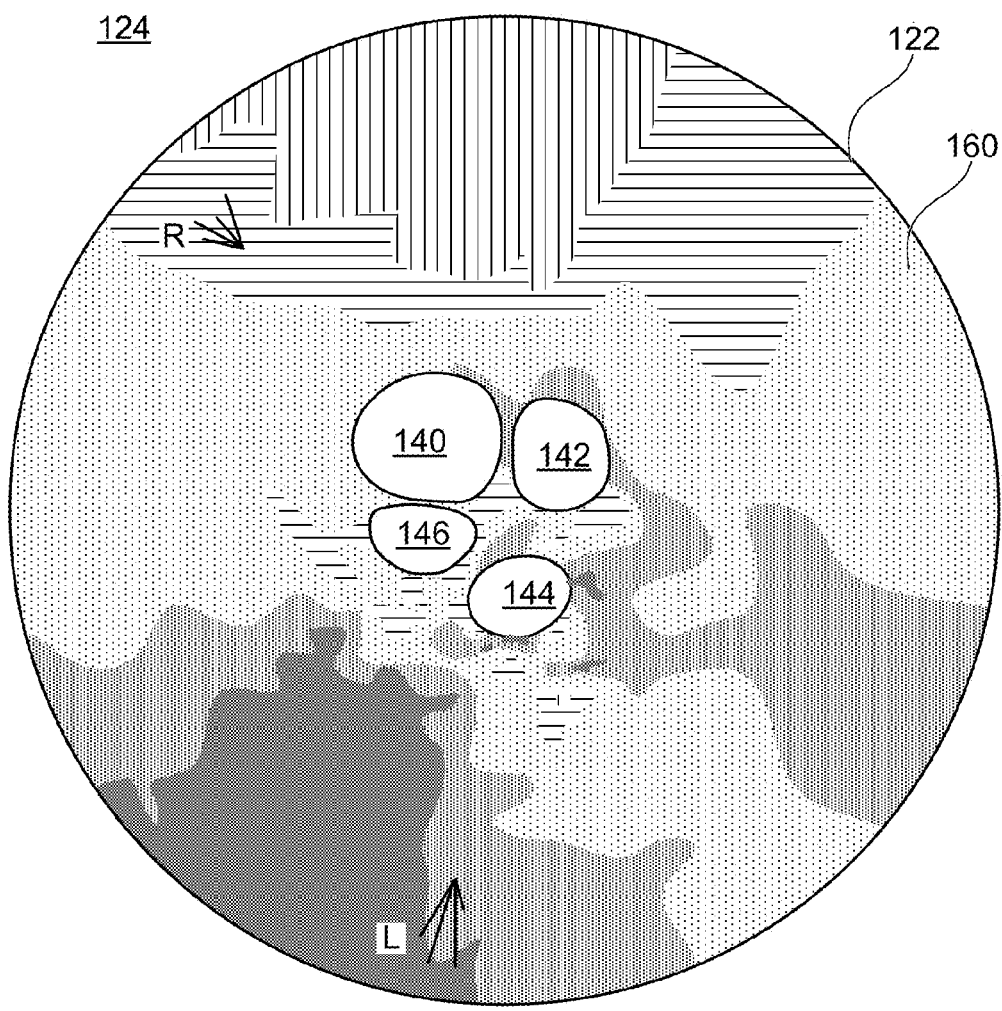
FIG. 3B is a schematic 2D map produced from the 2D mesh, according to embodiments of the present invention.

FIG. 3A is a schematic two-dimensional (2D) mesh 120 derived from 3D mesh 70, and FIG. 3B is a schematic 2D map 160 produced from 2D mesh 120, according to embodiments of the present invention. Processor 30 derives 2D mesh 120 from 3D mesh 70 by initially selecting one of the openings in the 3D mesh. The selected opening is herein referred to as the 2D mesh defining opening, or just as the defining opening. In the following description, the defining opening is assumed to comprise opening 72, which has 3D perimeter 74, corresponding to open mitral valve 64.

To produce 2D mesh 120, the processor transforms perimeter 74 into a 2D closed boundary 122 in a plane 124. In FIG. 3A plane 124 corresponds to the plane of the paper. The transformation from perimeter 74 to 2D closed boundary 122 is a one-to-one mapping which maps each point on the perimeter to a corresponding point on the 2D boundary. The 2D boundary may be the boundary of any convenient closed figure, and is herein assumed by way of example to be a circle, so that boundary 122 is also referred to herein as circle 122. Topologically 2D boundary 122 divides the plane it defines, plane 124, into an interior region 126 of the plane and an exterior region 128 of the plane.

Once processor 30 has produced 2D boundary 122, it performs an overall mapping of each of the line segments and junctions of 3D mesh 70 into interior region 126. The overall mapping comprises a one-to-one mapping for the colored line segments, and a one-to-one mapping for the colored junctions. In addition, the overall mapping is structured so that the connectivity between the colored line segments and the colored junctions of the 3D colored mesh is maintained in 2D mesh 120. In one embodiment the connectivity is maintained by adjusting magnifications of the triangles produced by the line segments of the 3D colored mesh. In other words, a given triangle in the 3D colored mesh is mapped to a geometrically similar triangle in 2D mesh 120.

The overall mapping preserves the number of openings, other than the defining opening, that are in 3D mesh 70. Thus, four 3D pulmonary vein openings 78, 82, 86, and 88 of 3D mesh 70 respectively map to four 2D openings 140, 142, 144, and 146 in 2D mesh 120.

Processor 30 generates 2D map 160 from 2D mesh 120 by filling in the triangles of 2D mesh 120 with appropriate colored surfaces.

Figure 4A:
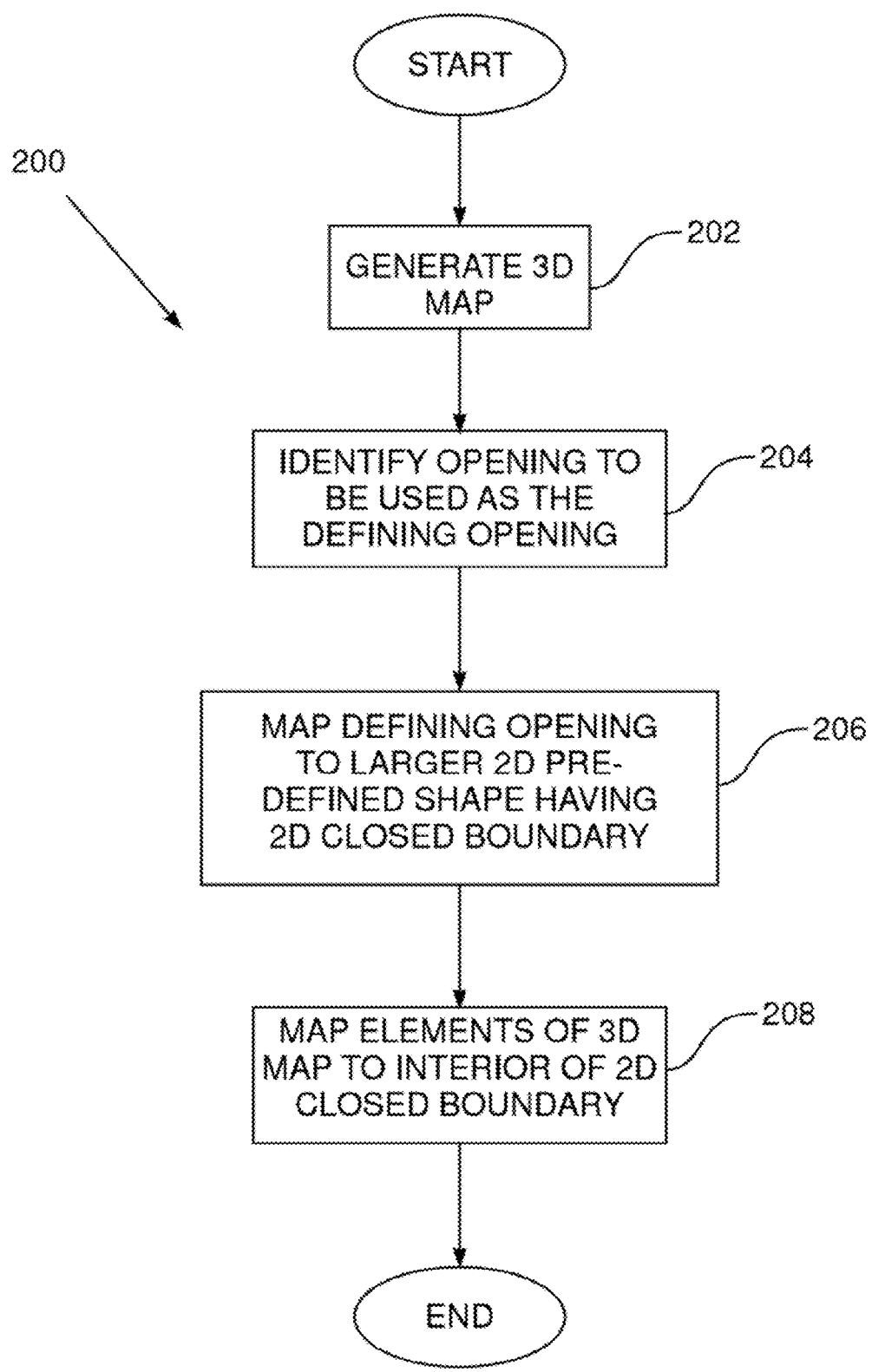
FIG. 4A is a flowchart of steps performed in generating a 2D map.
Figure 4B:
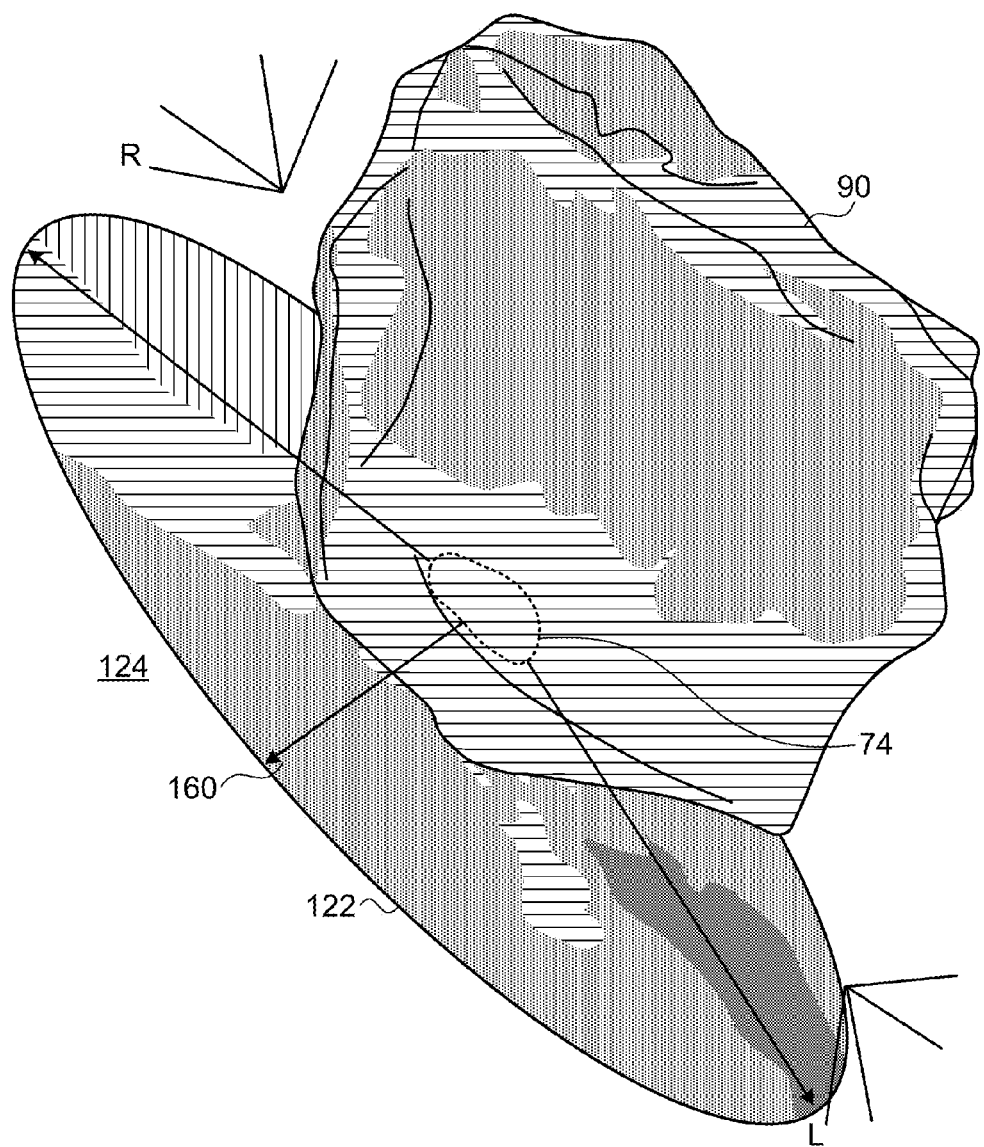
FIG. 4B is a schematic figure illustrating the steps, according to embodiments of the present invention.

FIG. 4A is a flowchart 200 of steps performed in generating 2D map 160 from 3D map 90, and FIG. 4B is a schematic figure illustrating the steps, according to embodiments of the present invention. In FIG. 4B plane 124 of 2D map 160 has been rotated so that is no longer in the plane of paper, and so that circle 122 appears as an ellipse. In addition, 3D map 90 has been rotated so that 3D perimeter 74 is at the "back" of the map, and so the perimeter has been drawn as a dashed figure.

In a map step 202, processor 30 generates 3D map 90, generally as described above with respect to FIGS. 2A and 2B. Thus, the processor measures locations of a multiplicity of points on a cavity, together with LATs at the points. The processor generates a 3D mesh having the locations and values of the LATs incorporated into the mesh. The processor then produces a 3D map from the 3D mesh.

In an opening selection step 204, processor 30 selects an opening in the 3D map, or the equivalent opening in the 3D mesh generating the 3D map, as a defining opening. For simplicity, the defining opening is assumed to be opening 72, corresponding to open mitral valve 64, having 3D perimeter 74.

In an opening mapping step 206, the processor maps the defining opening to a larger 2D closed boundary having a pre-defined shape, herein by way of example assumed to be a circle. The mapping of the defining opening to the closed boundary is described in more detail with respect to FIG. 3A above. As illustrated by the arrows in FIG. 4B from perimeter 74 to boundary 122, the mapping may be thought of as "stretching" the defining opening to the larger 2D closed boundary.

In a map generation step 208, the processor maps elements of 3D map 90 to the 2D interior region of the 2D closed boundary. Typically the mapping of the elements of the 3D map is performed by mapping the line segments and junctions of the mesh forming the 3D map to the interior region of the 2D closed boundary. The mapped line segments and junctions are then used, as described above with reference to FIG. 3A and FIG. 3B, to generate 2D map 160. The mapping performed in step 208 may be thought of as "flattening" a "dome-like" 3D cavity based on the defining opening, herein the open mitral valve, into a 2D region within the pre-defined 2D closed boundary.

Figure 5A:
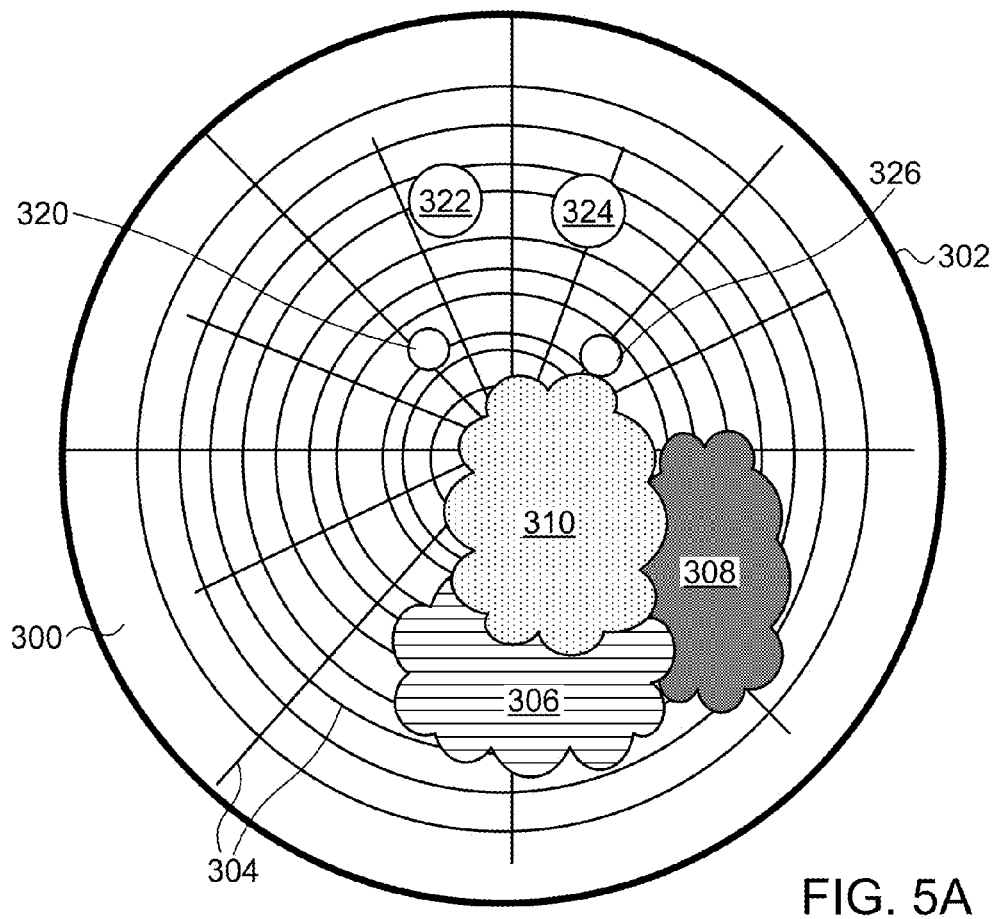
FIGS. 5A and 5B are schematic figures illustrating use of the organ visualization system, according to embodiments of the present invention.
Figure 5B:
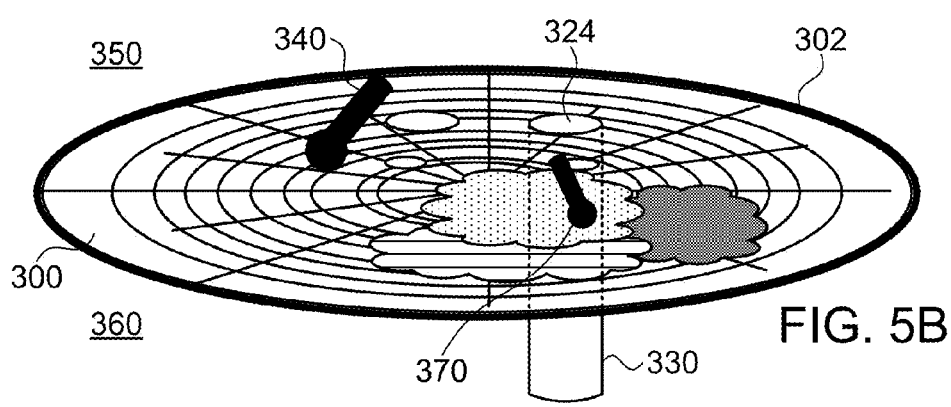

FIGS. 5A and 5B are schematic figures illustrating use of system 20, according to embodiments of the present invention. FIG. 5A illustrates a schematic 2D map 300 of left atrium 28, the map having a defining opening based on open mitral valve 64. Processor 30 formulates 2D map 300 substantially as described above, so that the 2D map has a 2D closed boundary 302. By way of example, boundary 302 is assumed to be in the form of a circle. Grid lines 304, of circles and straight lines, have been constructed in the map for the purposes of locating map details. Four pulmonary vein openings 320, 322, 324, and 326 are drawn in 2D map 300. In FIG. 5A the plane of 2D map 300 corresponds to the plane of the paper.

By way of example, 2D map 300 has three differently colored sections 306, 308, and 310, representing different values of LAT at the locations indicated by the grid lines the sections cover. Known configurations of LATs may occur in tachycardia situations, and the representation of the LATs on 2D map 300, such as is exemplified by sections 306, 308, and 310, allows operator 26 to identify the site causing the tachycardia.

In FIG. 5B the plane of 2D map 300 has been rotated so that it is no longer in the plane of the paper, and so that the map appears as an ellipse, i. e., as a perspective view of the 2D map. The amount of rotation may be set by operator 26, and the rotated map may be displayed on screen 44. This type of rotation allows the 2D map to be used as a bounding surface having two sides. A region 350 in contact with one side of the 2D map corresponds to the interior of the left atrium. A region 360 in contact with the other side of the 2D map corresponds to the exterior of the left atrium. As is explained in more detail below, elements on either side of the plane of the map, corresponding to physical elements present in the interior or the exterior regions of the left atrium 28, may be drawn on the map, and the presentation of such elements in registration with the map aids operator 26 in visualizing the left atrium.

The plane of the 2D map may be rotated to any convenient orientation, according to the requirements of operator 26. For example, the plane may be rotated so that it is vertical on screen 44, with region 350, the left atrium interior, on the left side of the screen, and with region 360, the left atrium exterior on the right side of the screen. Such a configuration is referred to herein as a "sideways" view. Alternatively, the plane may be rotated so that region 350 is on the lower part of the screen, and so that region 360 is on the upper part of the screen. Such a configuration is referred to herein as an "upside-down" view. Further alternatively, the plane may be rotated as illustrated in FIG. 5B, with region 350 being above the 2D map, and with region 360 being below the map. Such a configuration is referred to herein as an "upright" view, and is illustrated by FIG. 5B. The following examples refer to the upright view configuration.

By way of example, one of the pulmonary veins entering the left atrium, from the exterior of the left atrium has been schematically drawn as a cylinder 330 connected to opening 324. Cylinder 330 has been drawn beneath the plane of 2D map 300, in region 360.

In addition, an icon 340, representing distal end 62 of catheter 60 (FIG. 1) has been drawn above the plane of 2D map 300, in region 350. Since the location and orientation of the distal end are known, the location and orientation of icon 340 with respect to 2D map 300 may be visually indicated on the map. For example, operator 26 may desire that distal end 62 is orthogonal to a region of the surface of the left atrium it is closest to, in preparation for contacting the region so as to ablate the region. Drawing the location and the orientation of icon 340 with respect to map 300 enables the operator to quickly judge if the distal end is correctly positioned with respect to the region.

As a further example, a second icon 370 has been drawn within cylinder 330 and in region 360. Icon 370 may be drawn to represent the location and orientation of the distal end of a second catheter (not shown in FIG. 1) within the pulmonary vein (exterior to the left atrium) represented by cylinder 330.

It will be understood that configurations other than that illustrated in FIG. 5B are possible. For example, the elements in FIG. 5B could be rotated to a sideways view, or to an upside-down view. All such configurations are assumed to be comprised within the scope of the present invention.

Figure 6:
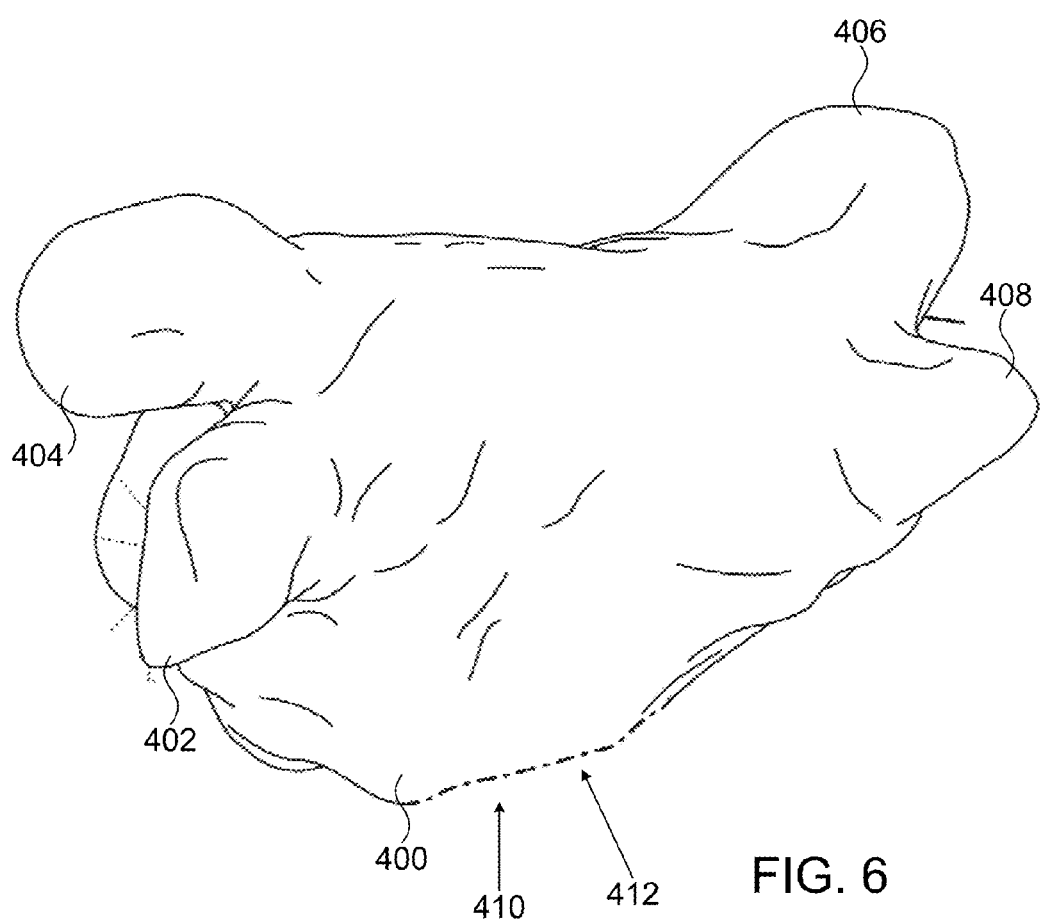
FIGS. 6, 7, and 8 are schematic diagrams of a left atrium with different views, according to embodiments of the present invention.
Figure 7:
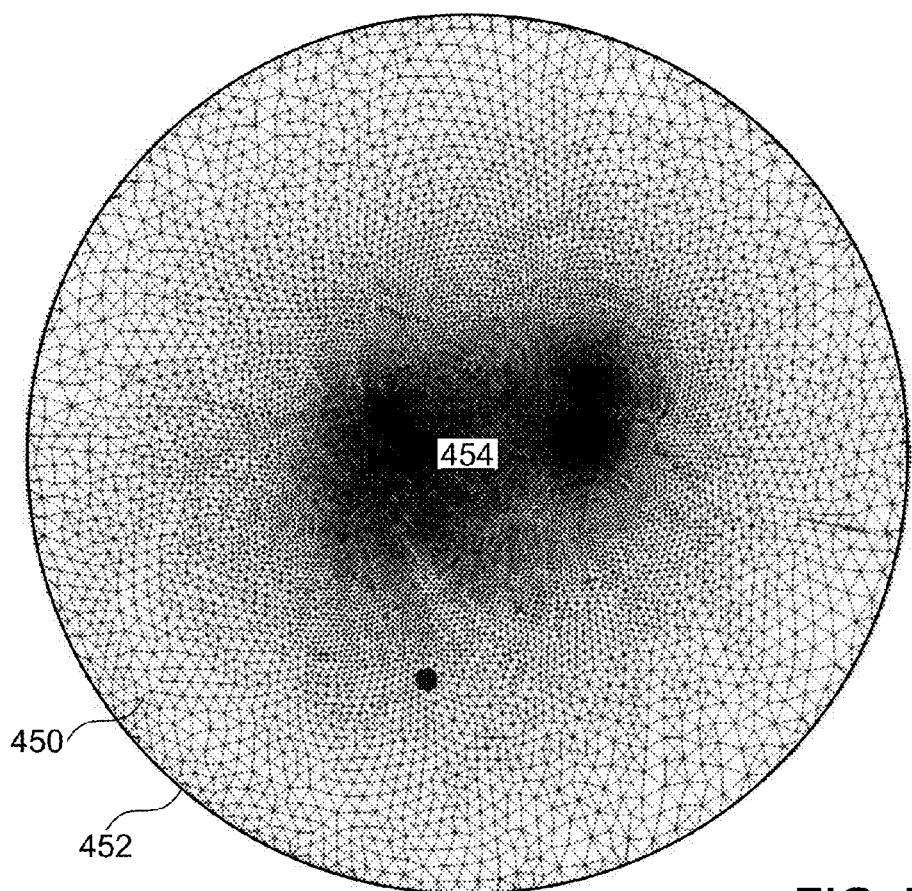
Figure 8:
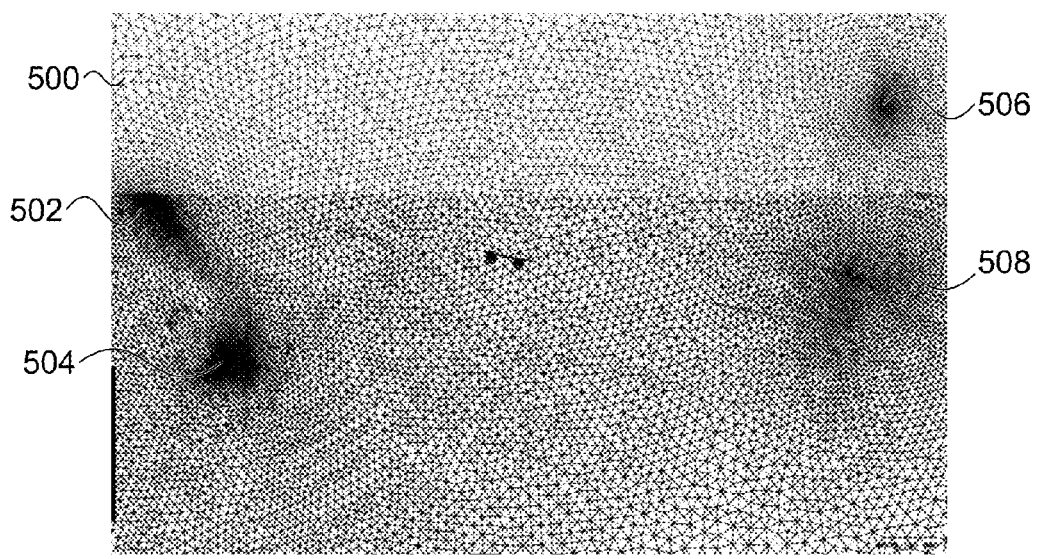

FIGS. 6, 7, and 8 are schematic diagrams of different views of left atrium 28, according to embodiments of the present invention.

FIG. 6 is a schematic 3D map 400 of the left atrium, the map illustrating the 3D locations of the left atrium surface. Map 400 has been generated without incorporating values of LATs into the map, so that the map may be presented on screen 44 as a 3D gray scale map. Map 400 is generated from a 3D mesh, generally as described above for 3D map 90; for simplicity the 3D mesh is not shown in the figures.

In contrast to the representations of the left atrium in FIGS. 2A-5B, openings in left atrium 28 to the pulmonary veins are not shown as open figures. Rather, the openings for the pulmonary veins appear as protrusions 402, 404, 406, and 408 in the 3D map surface. A mitral valve opening 410, having a 3D perimeter 412, is at the bottom of 3D map 400. (Opening 410 is in the "back" of map 400.)

FIG. 7 is a 2D mesh 450 of the left atrium, and FIG. 8 is an enlarged 2D view 500 of a section of mesh 450. 2D mesh 450 is produced substantially as described above by flowchart 200 (without filling in the spaces of the mesh) so that a circular boundary 452 is mapped from perimeter 412. Protrusions 402, 404, 406, and 408 appear as a dense region 454 in mesh 450.

Enlarged view 500 provides structure to region 454, so that protrusions 402, 404, 406, and 408 now appear as well separated dense regions 502, 504, 506, and 508.

It will be understood that 2D and 3D diagrams exemplified by FIGS. 2B, 3B, 4B, 5A, 5B, and 6-8 may be presented on screen 44. In some embodiments more than one diagram may be displayed simultaneously. For example, operator 26 may choose to display the 3D map of FIG. 2B at the same time as displaying the corresponding 2D map of FIG. 3B. Alternatively, rather than displaying complete 2D and 3D maps, operator 26 may choose to display only part of a map. For example, returning to FIGS. 5A and 5B, there is a corresponding 3D map. When displaying FIG. 5B, the operator may choose to display a part of the corresponding 3D map in the vicinity of distal end 62, i.e., in the region of icon 340. Typically, the 3D map part may be displayed as a window in screen 44 while the screen shows rotated 2D map 300.

A magnified view exemplified by enlarged view 500 (FIG. 8) may be applied to other 2D maps generated by system 20. For example, returning to FIG. 3B, operator 26 may magnify a region around one of the pulmonary vein openings, so as inspect LATs of the region more exactly. Such a local magnified view may be applied by the operator moving a cursor to the region, so that in that location the display becomes locally magnified.

In some embodiments the 2D maps produced by system 20 may incorporate more than one characteristic into the map. The description above has exemplified incorporating LAT values into the map. Other characteristics that may be incorporated comprise electro-potentials, temperature, force, tissue thickness, tissue contractility, tissue impedance or characteristics derived from these or other factors. The incorporation may be by means of colors, gray scales, hatching, shading, or marking of contours indicative of levels of the characteristic being depicted. Alternatively, such as if tissue thickness is incorporated, a 2D map such as map 160 may be transformed into a "pseudo-2D" map, by adding a tissue thickness indication to the map. The indication may, for example, comprise adding numerical values to the map. Alternatively or additionally, the indication may comprise adding height changes above plane 124 of the map. Such a height change will become visible as the plane of the map is rotated, to a view such as is shown in FIG. 5B.

The embodiments described above have used the mitral valve, in its opened state, as the defining opening of the left atrium. It will be understood that other openings of the left atrium may be used as the defining opening, for example one of the pulmonary vein openings.

It will also be understood that chambers of the heart other than the left atrium may be used as the chamber being imaged. For example, the right atrium, or one of the ventricles may be imaged, using an appropriate defining opening for the selected chamber. For example, if the right atrium is imaged, the open tricuspid valve may be used as the defining opening.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising:
    inserting a distal end of a catheter into a three-dimensional (3D) heart chamber, wherein the distal end of the catheter comprises at least one sensor;
    measuring a characteristic of the heart chamber with the at least one sensor;
    integrating the measured characteristic with a location of the distal end of the catheter to create a plurality of points;
    generating a 3D mesh from the plurality of points, the 3D mesh formed from a plurality of line segments and junctions having a connectivity, the 3D mesh including an opening defined by a closed perimeter, the opening in the 3D mesh corresponding to an anatomical opening in a heart;
    generating a 3D map from the 3D mesh, the 3D map illustrating the characteristic, measured by the catheter, of a 3D heart chamber, the 3D map including an opening corresponding to the opening in the 3D mesh, the opening in the 3D map having the same perimeter as the perimeter of the corresponding opening in the 3D mesh;
    generating a two-dimensional (2D) mesh by mapping each point on the perimeter of the opening on the 3D mesh to a corresponding point on a 2D closed boundary, the 2D closed boundary having a perimeter corresponding to the perimeter of the corresponding opening on the 3D mesh, the 2D boundary being larger than the corresponding opening on the 3D mesh;
    mapping each of the line segments and junctions of the 3D mesh into an interior of the 2D boundary of the 2D mesh while maintaining the connectivity of the 3D mesh in the 2D mesh; and
    generating, from the 2D mesh, a 2D map corresponding to the boundary and interior of the 2D mesh so as to generate a 2D map of the characteristic of the 3D heart chamber.

2. The method according to claim 1, wherein the heart chamber comprises a left atrium of a heart.

3. The method according to claim 2, wherein the anatomical opening comprises an open mitral valve of the heart.

4. The method according to claim 2, wherein the anatomical opening comprises a pulmonary vein opening to the left atrium.

5. The method according to claim 1, wherein the characteristic comprises one of a local activation time (LAT) of the heart chamber, a force acting on the heart chamber, and a temperature of the heart chamber.

6. The method according to claim 1, wherein the 2D closed boundary comprises a circle.

7. The method according to claim 1, wherein the 2D map defines a plane, and wherein the 2D map is rotatable about a line in the plane so as to present a perspective view of the 2D map, and wherein a first region in contact with a first side of the plane corresponds to an interior region of the 3D heart chamber, and a second region in contact with a second side of the plane corresponds to an exterior region of the 3D heart chamber.

8. The method according to claim 7, wherein a distal end of a catheter is located in the interior region at a distance and having an orientation with respect to the 3D heart chamber, and wherein an icon representative of the distance and the orientation is positioned in the first region with respect to the plane.

9. The method according to claim 7, wherein the 3D heart chamber comprises a left atrium, and wherein a pulmonary vein connects to the exterior region of the left atrium via a vein opening, the method further comprising generating in the 2D map an indication of the vein opening, and positioning in the second region a representation of the pulmonary vein connected to the indication.

10. The method according to claim 9, wherein a distal end of a catheter is located within the pulmonary vein, and wherein an icon representative of a distance and a location of the distal end is positioned within the second region.

11. The method according to claim 1, and comprising incorporating an indication of respective tissue thicknesses of elements of the heart chamber into the 2D map.

12. An apparatus, comprising:
    a processor; and
    a non-transitory computer readable medium storing a plurality of instructions, which when executed, cause the processor to:
    integrate a measured characteristic of a three dimensional (3D) heart chamber having an anatomical opening, the characteristic being measured by a distal end of a catheter inserted into the 3D heart chamber, the distal end having at least one sensor,
    generate a 3D mesh from the plurality of points, the 3D mesh formed from a plurality of line segments and junctions having a connectivity, the 3D mesh including an opening defined by a closed perimeter, the opening in the 3D mesh corresponding to the anatomical opening in a heart;
    generate a 3D map from the 3D mesh, the 3D map illustrating the characteristic, measured by the distal end of the catheter in the 3D heart chamber, the 3D map including an opening corresponding to the opening in the 3D mesh, the opening in the 3D map having the same perimeter as the perimeter of the corresponding opening in the 3D mesh;

generate a two-dimensional (2D) mesh by mapping each point on the perimeter of the opening on the 3D mesh to a corresponding point on a 2D closed, the 2D closed boundary having a perimeter corresponding to the perimeter of the corresponding opening on the 3D mesh, the 2D boundary being larger than the corresponding opening on the 3D mesh; and map each of the line segments and junctions of the 3D mesh into an interior of the 2D boundary of the 2D mesh while maintaining the connectivity of the 3D mesh in the 2D mesh; and generate, from the 2D mesh, a 2D map corresponding to the boundary and interior of the 2D mesh so as to generate a 2D map of the characteristic of the 3D heart chamber.

13. The apparatus according to claim 12, wherein the heart chamber comprises a left atrium of a heart.

14. The apparatus according to claim 13, wherein the anatomical opening comprises an open mitral valve of the heart.

15. The apparatus according to claim 13, wherein the anatomical opening comprises a pulmonary vein opening to the left atrium.

16. The apparatus according to claim 12, wherein the characteristic comprises one of a local activation time (LAT) of the heart chamber, a force acting on the heart chamber, and a temperature of the heart chamber.

17. The apparatus according to claim 12, wherein the 2D closed boundary comprises a circle.

18. The apparatus according to claim 12, wherein the 2D map defines a plane, and wherein the 2D map is rotatable about a line in the plane so as to present a perspective view of the 2D map when displayed on the screen and wherein a first region in contact with a first side of the plane corresponds to an interior region of the 3D heart chamber.

19. The apparatus according to claim 18, wherein a distal end of a catheter is located in the interior region at a distance and having an orientation with respect to the 3D heart chamber, and wherein an icon representative of the distance and the orientation is positioned in the first region with respect to the plane.

20. The apparatus according to claim 18, wherein the 3D heart chamber comprises a left atrium, and wherein a pulmonary vein connects to the exterior region of the left atrium via a vein opening, the method further comprising generating in the 2D map an indication of the vein opening, and positioning in the second region a representation of the pulmonary vein connected to the indication.

21. The apparatus according to claim 20, wherein a distal end of a catheter is located within the pulmonary vein, and wherein an icon representative of a distance and a location of the distal end is positioned within the second region.

22. The apparatus according to claim 12, wherein the instructions, when executed, further cause the processor to incorporate an indication of respective tissue thicknesses of elements of the heart chamber into the 2D map.

* * * * *